United States Patent [19]
Boross et al.

[11] Patent Number: 4,650,762
[45] Date of Patent: * Mar. 17, 1987

[54] ISOLATION OF CARBOXYPEPTIDASE B ENZYME

[75] Inventors: László Boross; Erzsébet Dala née Rezneki, both of Budapest; Aranka Kiss née Deér, Szeged; Béla Szajáni; Árpád Tetzli, both of Budapest, all of Hungary

[73] Assignee: Reanal Finomvegyszergyar, Budapest, Hungary

[*] Notice: The portion of the term of this patent subsequent to Jul. 30, 2002 has been disclaimed.

[21] Appl. No.: 595,767

[22] Filed: Apr. 2, 1984

[30] Foreign Application Priority Data

Jul. 11, 1983 [HU] Hungary ............... 2469/83

[51] Int. Cl.⁴ ............. C12N 11/08; C12N 11/06; C12N 9/64
[52] U.S. Cl. ............................ 435/180; 435/181; 435/226; 435/814; 435/816
[58] Field of Search ............... 435/212, 226, 177, 180, 435/181, 814, 816

[56] References Cited
U.S. PATENT DOCUMENTS 3,260,654  7/1966  Toccaceli ........................... 435/226
3,357,894 12/1967  Uriel et al. ......................... 435/226
3,625,829 12/1971  Schmidt-Kaster et al. ......... 435/226
4,415,667 11/1983  Koide et al. ..................... 435/226 X
4,532,214  7/1985  Szajani et al. ...................... 435/228

OTHER PUBLICATIONS

Folk, et al., J. Biol. Chem., vol. 235, No. 8, 1960, pp. 2272–2277.
Chibata, I., Immobilized Enzymes, John Wiley & Sons, N.Y., 1978, pp. 31–33.
Dixon, et al., Enzymes, Academic Press Inc., N.Y., 1964, pp. 27–48.
Marinkovic, et al., Biochem. J., vol. 163, 1977, pp. 253–260.

Primary Examiner—David M. Naff
Attorney, Agent, or Firm—Gabriel P. Katona

[57] ABSTRACT

Carboxypeptidase B enzyme is isolated by a process wherein homogenized and autolyzed pancreas is subjected to a thermal treatment, and carboxypeptidase B is separated by fractionation with ammonium sulfate. This process produces carboxypeptidase B having satisfactory specific activity while eliminating the use of pancreas cell fluid or an acetonous powder from pancreas as a starting material. The isolated carboxypeptidase B may be immobilized on a polymer gel containing carboxy groups activated with a carbodiimide.

8 Claims, No Drawings

ISOLATION OF CARBOXYPEPTIDASE B ENZYME

This invention relates to a process for the isolation of carboxypeptidase B enzyme from the pancreas of mammals, particularly from the pancreas of swine.

The commercially available carboxypeptidase B enzyme is isolated from the pancreas of swine but according to further known methods the carboxypeptidase B enzyme can be isolated from the pancreas of other mammals /e.g. cattle, goat / too.

According to the article published in J. Biol. Chem. 25, 2272 /1960/ the pancreas of swine is sliced and subjected to autolysis at room temperature. The fat content of the pancreas is removed by treatment with acetone, a mixture of acetone and ether and finally with ether, the thus degreased organ is dried and powdered. The acetoneous powder is extracted with water and the extract is fractionated with ammonium sulfate. After desalinization the protein solution is subjected to ion exchange by admixture with DEAE-cellulose. After elution the fraction containing the carboxypeptidase B enzyme is subjected to further fractionation with ammonium sulfate. After desalinization a further ion exchange with DEAE-cellulose by column chromatography is carried out and the product is again precipitated with ammonium sulfate. The precipitate is desalinized by dialysis or gel filtration. The product is stored in frozen state because liophylization causes an inactivation of 25–45%.

The specific activity of the product amounts to 184.2 units/mg/measured on a hippuryl-L-arginine substrate at 25° C./ which corresponds to a 16-17-fold purification as compared to the extract prepared from the autolysed tissue.

Nowadays in practice the above process is most widespreadly used.

According to the article published in Biochemistry 1, 1069 /1962/ carboxypeptidase B of cattle bovine pancreas is prepared in crystalline form by activating the purified zimogene i.e. the procarboxypeptidase B. In this process also the aqueous extract of the acetoneous powder of pancreas is used for the isolation of zimogene. The aqueous extract contains the procarboxypeptidase B which is purified by means of chromatography first on DEAE-cellulose and thereafter on DEAE-Sephadex. The procarboxypeptidase B is converted into active carboxypeptidase B with the aid of tripsine and is finally crystallized.

According to the article published in Biochem. J. 163, 253 /1977/ carboxypeptidase B enzyme is isolated from human pancreas. The preparation of the acetoneous powder, the precipitation with ammonium sulfate and the DEAE-cellulose chromatography are carried out substantially as described in J. Biol. Chem. 235, 2272 /1960/. The said process is modified only in the concentration of the buffer and the elution gradient used at the DEAE-cellulose chromatography. The carboxypeptidase B is then separated into two fractions—namely to fractions $B_1$ and $B_2$—by means of chromatography on Whatman CM-cellulose 32 ion-exchanger. The specific activity of the $B_1$ fraction amounts to 1192 unit/mg /measured at 37° C. on a hippuryl-L-arginine substrate/ while that of the $B_2$ fraction is 862 units/mg; this corresponds to a 108-fold and 78-fold purification, respectively, as compared to the aqueous extract.

According to Indian J. Biochem. Biphys. 12, 24 /1975/ and 13, 106 /1976/ carboxypeptidase B can be isolated from goat pancreas. The main features of this process can be summarized as follows:

The goat pancreas is frozen at −20° C., sliced in frozen state, the sliced pancreas is allowed to warm up to +4° C. and the cell fluid which pours out is collected. The collected cell fluid is allowed to autolyse. The pH of the solution is adjusted to 4.6, the solution is diluted to 10-fold of its volume with distilled water and the suspension thus formed is allowed to stand at +4° C. for 2-3 hours. The overwhelming amount of the active carboxypeptidase precipitates. This product is extracted with barium hydroxide at a pH of 10.0–10.4, the enzyme is crystallized from the extract at a pH value of 6.5 and recrystallized four times. Further purification of this product is described in Indian J. Biochem. Biophys. 13, 106 /1976/. For this purpose the substance precipitated at a pH value of 6.5 is dissolved in 0.2 molar barium hydroxide, the pH of is adjusted to 7.0 with acetic acid and the product is further purified by fractionating with ammonium sulfate and by repeated ion-exchange on DEAR-cellulose. The desalinated enzyme solution is stored at −20° C. The specific activity of the product amounts to 102.66 units/mg /measured on a hippuryl-L-arginine substrate/ which corresponds to a 44-fold purification.

According to J. Mol. Catal. 10, 253 /1981/ the aqueous extract of the acetoneous powder of goat pancreas is fractionated with ammonium sulfate and the fraction obtained at a 0.3–0.8-fold saturation is subjected to chromatography on CM-Sephadex C-50 and DEAE-cellulose. The specific activity of the product amounts to 82.9 units/mg / measured on hippuryl-L-arginine substrate/ which corresponds to a 18.2-fold purification.

The common drawback of the above known methods resides in the fact the cell fluid of pancreas or the acetonous powder of the said organ is used as starting material. The collection of the cell fluid is difficult and circumstantial; in the case of swine pancreas it is even practically impossible because of the high fat and mucilage content of the organ. The preparation of the acetoneous powder is expensive and requires the use of solvents involved with a high risk of fire and explosion /e.g. ether, acetone/:, moreover local warming-up might damage the enzyme and decrease the yield and specific activity. A further disadvantage is that a product of satisfactory purity can only be obtained by means of a complicated multi-step series of operation.

The object of the present invention is to overcome the above drawbacks of the known methods and to provide a simple readily feasible process for the preparation of carboxypeptidase B of satisfactory specific activity under eliminating the collection of cell fluid and also the preparation of the acetoneous powder.

It has been found that an enzyme solution having a minimal specific activity of 70 units/mg /measured at 25° C., on a hippuryl-L-arginine substrate/ which can be directly used for the preparation of immobilized carboxypeptidase B without further purification can be obtained by subjecting homogenised swine pancreas to thermal treatment after autolysis, centrifuging or filtering, saturating the supernatant with the salt of a monovalent cation formed with an inorganic acid in two steps, separating the precipitate from the suspension obtained in the second saturation step and subjecting the solution of the precipitate to dialysis against water.

According to the present invention there is provided a new process for the isolation of carboxypeptidase B enzyme from mammal pancreas which comprises homogenizing mammal pancreas in a manner known per se, subjecting the homogenized pancreas to autolysis at 37° C. for an hour or at 25° C. for 16 hours, diluting the autolysed product with a buffer having a pH value of 5.0–8.5 in a 1:1 ratio, subjecting the product to thermal treatment at 50°–70° C. for 5–30 minutes, centrifuging or filtering the heat-treated mixture, adding 200–320 g/l of ammonium sulfate to the supernatant, centrifuging the suspension obtained, discarding the precipitate, precipitating the active fraction which comprises the carboxypeptidase B enzyme by adding ammonium sulfate to the supernatant in an amount of 10–80 g/l, dissolving the enzyme separated by centrifuging in water or a buffer solution, dialysing the solution thus obtained against water or a buffer solution and storing the enzyme in frozen state.

According to the process of the present invention the homogenized and autolysed mammal pancreas is diluted with a buffer having a pH value of 5.0–8.5 /preferably pH 6.0/ in a ratio of 1:1, whereupon it is subjected to thermal treatment at 50°–75° C. for 5–30 minutes. It is preferred to carry out thermal treatment at 60° C. for 20 minutes. As a result of the said thermal treatment the majority of the proteins which accompany the enzyme to be isolated is denaturated. The denaturated protein precipitates from the aqueous solution in the form of a precipitate having a large surface and it entrains the larger part of the impurities being present in the solution due to its clarifying effect. Thus the complicated and expensive step of the preparation of the acetoneous powder of pancreas is eliminated.

A significant part of the contaminating proteins is precipitated from the buffer solution obtained after removing the denaturated protein by adding 200–300 g/l— preferably 310–320 g/l—of ammonium sulfate. The precipitate containing the contaminating proteins is removed and from the supernatant liquid the product containing the enzyme is precipitated by adding 10–80 g/l—preferably 30 g/l—of ammonium sulfate. The precipitate is dissolved in water or a buffer solution and the solution thus obtained is dialysed against water in a manner known per se. The minimal activity of the product containing the enzyme thus obtained amounts to 70 units/mg /measured at 25° C./ which corresponds approximately to a 120-fold purification. This product can be used e.g. for the preparation of immobilized enzyme compositions directly i.e. without further purification.

The immobilized carboxypeptidase B compositions can be used for the determination of COOH terminal amino acids of proteins and peptides and also for the industrial scale resolution of D,L-arginine and D,L-lysine. This enzyme could not be hitherto used for the latter purpose because of the circumstantial and expensive manufacturing process of the enzyme. The new process of the present enzyme provides a simple and readily feasible method for the isolation of the enzyme, it enables the immobilization of the enzyme in active form and also the realization of a continuous process.

A further object of the present invention is the preparation of an immobilized carboxypeptidase B enzyme which is suitable for the achievement of the above purposes. According to this feature of the present invention there are prepared immobilized carboxypeptidase B enzyme compositions which are suitable for long-lasting use and comprise the enzyme in a form bound to a carrier in a manner which is chemically inert, unlimitedly resistant to the effect of microorganisms and ensures a high flow velocity. It is a further requirement that the enzyme should be bond to the carrier under mild reaction conditions.

It has been found that polymer gels comprising at least 0.1 m-equivalent/g—preferably 2-8 m-equivalent/g—of functional carboxy groups and formed from an acrylic acid and/or methacrylic acid, an acrylamide and/or methacrylamide monomer with the aid of a cross-linking agent of the acrylic or allylic type /e.g. N,N'-methylene-bis-acrylamide, ethylene diacrylate or N,N'-di-allyl-tartaric amide/ completely comply with the requirements raised against carriers. The above enzyme carriers can be prepared by methods known per se.

The functional carboxy groups of the enzyme carriers can be activated by treatment with carbodiimide by methods known per se and can be made thus suitable for the binding of the carboxypeptidase B enzyme. This reaction can be accomplished under mild conditions /at 0°–4° C., pH=7.0/.

According to a further feature of the present invention there is provided a process for the preparation of an immobilized carboxypeptidase B enzyme composition which comprises treating a polymer gel which contains at least 0.1 m-equivalent/g of functional carboxy groups and is formed from acrylic acid and/or methacrylic acid, acrylic amide and/or methacrylic acid units by means of a cross-linking agent of the acrylic or allylic type with a carbodiimide compound being water-soluble or soluble in organic solvents at a temperature below 0° C., applying onto the thus activated carrier in a solution having a pH value of 4.5–8.5 carboxypeptidase B and washing and if desired drying the product thus obtained.

As polymer it is preferred to use the Akrylex C type polymers described above.

According to the process of the present invention carboxypeptidase B of whatever origin and isolated by any methods can be used.

As carbodiimide compound e.g. N-cyclohexyl-N'-[2-/4-morpholinyl/-ethyl]-carbodiimide-methyl-p-toluene-sulfonate or N-ethyl-N'-/3-dimethylaminopropyl/-carboxiimide-hydrochloride can be used for the activation of the carrier copolymer. It is preferred to use water-soluble compounds as carbodiimide component. From the compounds soluble only in organic solvents those derivatives can be used in the process of the present invention which are soluble in the given organic solvent in the cold /i.e. at a temperature below 0° C./.

The carboxypeptidase enzyme is applied onto the activated carrier in a solution having a pH value of 4.5–8.5—preferably between 6.0 and 7.0. As reaction medium preferably a 0.05–0.1 molar potassium phosphate buffer having a pH of 7.0 can be used.

The immobilized enzyme composition prepared by the above coupling reaction is washed in a manner known per se and if desired dried. The enzyme composition can be however stored at a temperature of 0°–4° C. in aqueous suspension too.

The specific activity of the immobilized enzyme composition of the present invention amounts to 600–900 μmoles of hydrolysed hippuryl-L-arginine/minute/mg xerogel; this value is very advantageous from the point of view of practical applicability.

Further details of the process of the present invention are to be found in the following Examples without limiting the scope of protection to the said Examples.

EXAMPLE 1

0.25 kg of swine pancreas is minced on a meat-chopper, whereupon 250 ml of a 0.05 molar tris-HCL buffer /pH 7.0/ are added and the mixture is allowed to stand at +4° C. overnight. Next day the suspension is warmed to 37° C. and allowed to stand at this temperature for an hour. The organ suspension is centrifuged, the supernatant is heated to 50° C. and incubated at this temperature for 30 minutes whereupon 2 parts by volume of icecold buffer are added and the mixture is centrifuged. To the supernatant 42.2 g of ammonium sulfate are added. The suspension is allowed to stand overnight, centrifuged, the precipitate is discarded, the pH of the supernatant is adjusted to 7.0–7.2 and 36.1 g of ammonium sulfate are added. The suspension is allowed to stand overnight and centrifuged. The precipitate is dissolved in a small amount of cold /+4° C./ tris-HCl buffer /pH 7.0/ and dialysed against distilled water until the salt is removed. After dialysis the solution is filtered and frozen. Thus 343 mg of carboxypeptidase B are obtained, specific activity 17.5 μmoles of hydrolysed hippuryl-L-arginine minute/mg protein.

EXAMPLE 2

0.25 kg of swine pancreas are minced on a meat-chopper, whereupon 250 ml of a 0.05 molar tris-HCl buffer /pH 7.0/ are added and the mixture is allowed to stand at +4° C. overnight. Next day the suspension is warmed to 37° C. and allowed to stand this temperature for an hour. The organ suspension is centrifuged, the supernatant is heated to 60° C. and incubated at this temperature for 10 minutes, whereupon 2 parts by volume, of icecold buffer are added and the mixture is centrifuged. To the supernatant 92 g of ammonium sulfate are added. Since while standing overnight no precipitate is formed, a further 78,7 g of ammonium sulfate are added to the solution after the pH had been adjusted to 7.0–7.2. The suspension is allowed to stand overnight and centrifuged. The precipitate is dissolved in a samll amount of cold /+4° C./ tris-HCl buffer /pH 7.0/ and dialysed against distilled water until the salt is removed. After dialysis the solution is filtered and frozen. Thus 295 mg of carboxypeptidase B are obtained. Specific activity: 53,1 μmoles of hydrolysed hippuryl-L-arginine minute/mg protein.

EXAMPLE 3

0.25 kg of swine pancreas are minced on a meat-chopper, whereupon 250 ml of a 0.05 molar tris-HCl buffer /pH 7.0/ are added and the mixture is allowed to stand at +4° C. overnight. Next day the suspension is warmed to 37° C. and allowed to stand this temperature for an hour. The organ suspension is centrifuged, the supernatant is heated to 60° C. and incubated at this temperature for 20 minutes, whereupon 2 parts by volume of icecold buffer are added and the mixture is centrifuged. To the supernatant 98,2 g of ammonium sulfate are added. Since while standing overnight no precipitate is formed, a further 86,9 g of ammonium sulfate are added to the solution after the pH had been adjusted to 7.0–7.2. The suspension is allowed to stand overnight and centrifuged. The precipitate is dissolved in a small amount of cold / +4° C./ tris-HCl buffer /pH 7.0/ and dialysed against distilled water until the salt is removed. After dialysis the solution is filtered and frozen. Thus 266 mg of carboxypeptidase B are obtained. Specific activity: 63,2 μmoles of hydrolysed hippuryl-L-arginine minute/mg protein.

EXAMPLE 4

0.25 kg of swine pancreas are minced on a meat-chopper, whereupon 250 ml of a 0.05 molar tris-HCl buffer /pH 7.0/ are added and the mixture is allowed to stand at +4° C. overnight. Next morning the suspension is warmed to 37° C. and allowed to stand at this temperature for an hour. The suspension is centrifuged, the supernatant is warmed to 75° C., incubated at this temperature for a further 5 minutes, whereupon 2 parts by volume of an icecold buffer are added and the mixture is centrifuged. To the supernatant 66,9 g of ammonium sulfate are added. Because during standing overnight no precipitate is formed, a further 55,8 g of ammonium sulfate are added to the solution, after the pH had been adjusted to 7.0–7.2. The suspension is allowed to stand overnight and centrifuged. The precipitate is dissolved in a small amount of cold /+4° C./ tris-HCl buffer pH 7.0/ and dialysed against distillated water until the salt is removed. After dialysis the solution is filtered and frozen. Thus 34 mg of carboxypeptidase B are obtained. Specific activity: 21,6 μmoles of hydrolysed hippuryl-L-arginine/minute/mg protein.

TABLE 1

Effect of the temperature and time of the thermal treatment of homogenised swine pancreas on the activity of the carboxypeptidase B

| Temperature (°C.) | Time (minute) | Total activity (*unit/kg pancreas) | Total protein (mg/kg pancreas) | Specific activity (unit/kg) |
| --- | --- | --- | --- | --- |
| 50 | 30 | 23968 | 1372 | 17.5 |
| 60 | 10 | 62660 | 1180 | 53.1 |
|  | 20 | 67260 | 1064 | 63.2 |
| 75 | 5 | 2932 | 136 | 21.6 |

*One unit is the amount of enzyme which catalyses the hydrolysis of 1.0 μmole of hippuryl-L-arginine/minute (measured at 25° C. and at pH 7.65)

EXAMPLE 5

0.25 kg of swine pancreas are minced on a meat-chopper and allowed to stand at room temperature overnight. Next day 250 ml of a 0.05 molar acetate buffer /pH 5.0/ are added, the suspension is heated to 60° C. and allowed to stand at this temperature for 20 minutes. After addition of 2 parts by volume of icecold water the mixture is centrifuged. To the supernatant 274.8 g of ammonium sulfate are added. The suspension is allowed to stand overnight, centrifuged and the precipitate is discarded. The pH of the supernatant is adjusted to 7.0–7.2 and 232.9 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 360 mg of carboxypeptidase B are obtained. Specific activity: 14.8 μmoles of hydrolysed hippuryl-L-arginine/minute/mg protein.

EXAMPLE 6

0.25 kg of swine pancreas are minced on a meat-chopper and allowed to stand at room temperature overnight. Next day 250 ml of a 0.05 molar acetate buffer /pH 5.5/ are added, the suspension is heated to 60° C.

and allowed to stand at this temperature for 20 minutes. After addition of 2 parts by volume of icecold water the mixture is centrifuged. To the supernatant 261.2 g of ammonium sulfate are added. The suspension is allowed to stand overnight, centrifuged and the precipitate is discarded. The pH of the supernatant is adjusted to 7.0–7.2 and 228 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 317 mg of carboxypeptidase B are obtained. Specific activity: 20.3 $\mu$moles of hydrolysed hippuryl-L-arginine/minute/mg protein.

EXAMPLE 7

0.3 kg of swine pancreas are minced on a meat-chopper and allowed to stand at room temperature overnight. Next day 300 ml of a 0.05 molar phosphate buffer /pH 6.0/ are added, the suspension is heated to 60° C. and allowed to stand at this temperature for 20 minutes. After addition of 2 part by volume of icecold water the mixture is centrifuged. To the supernatant 301 g of ammonium sulfate are added. The suspension is allowed to stand overnight, centrifuged and the precipitate is discarded. The pH of the supernatant is adjusted to 7.0–7.2 and 252.6 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 517 mg of carboxypeptidase B are obtained. Specific activity: 57 $\mu$moles of hydrolysed hippuryl-L-arginine/minute/mg protein.

EXAMPLE 8

0.3 kg of swine pancreas are minced on a meat-chopper and allowed to stand at room temperature overnight. Next day 300 ml of a 0.05 molar phosphate buffer /pH 6.5/ are added, the suspension is heated to 60° C. and allowed to stand at this temperature for 20 minutes. After addition of 2 part by volume of icecold water the mixture is centrifuged. To the supernatant 326 g of ammonium sulfate are added. The suspension is allowed to stand overnight, centrifuged and the precipitate is discarded. The pH of the supernatant is adjusted to 7.0–7.2 and 275.5 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 361 mg of carboxypeptidase B are obtained. Specific activity: 43.8 $\mu$moles of hydrolysed hippuryl-L-arginine/minute/mg protein.

EXAMPLE 9

0.3 kg of swine pancreas are minced on a meat-chopper and allowed to stand at room temperature overnight. Next day 300 ml of a 0.05 molar phosphate buffer /pH 7.0/ are added, the suspension is heated to 60° C. and allowed to stand at this temperature for 20 minutes. After addition of 2 parts by volume of icecold water the mixture is centrifuged. To the supernatant 326 g of ammonium sulfate are added. The suspension is allowed to stand overnight, centrifuged and the precipitate is discarded. The pH of the supernatant is adjusted to 7.0–7.2 and 272 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 488 mg of carboxypeptidase B are obtained. Specific activity: 39,9 $\mu$moles of hydrolysed hippuryl-L-arginine/minute/mg protein.

EXAMPLE 10

0.25 kg of swine pancreas are minced on a meat-chopper and allowed to stand at room temperature overnight. Next day 250 ml of a 0.05 molar tris-HCl buffer /pH 7.5/ are added, the suspension is heated to 60° C. and allowed to stand at this temperature for 20 minutes. After addition of 2 part by volume of icecold water the mixture is centrifuged. To the supernatant 247 g of ammonium sulfate are added. The suspension is allowed to stand overnight, centrifuged and the precipitate is discarded. The pH of the supernatant is adjusted to 7.0–7.2 and 202 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 695 mg of carboxypeptidase B are obtained. Specific activity: 17.4 $\mu$moles of hydrolysed hippuryl-L-arginine/minute/mg protein.

EXAMPLE 11

0.25 kg of swine pancreas are minced on a meat-chopper and allowed to stand at room temperature overnight. Next day 250 ml of a 0.05 molar tris-HCl buffer /pH 8.0/ are added, the suspension is heated to 60° C. and allowed to stand at this temperature for 20 minutes. After addition of 2 parts by volume of icecold water the mixture is centrifuged. To the supernatant 255 g of ammonium sulfate are added. The suspension is allowed to stand overnight, centrifuged and the precipitate is discarded. The pH of the supernatant is adjusted to 7.0–7.2 and 198 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 552 mg of carboxypeptidase B are obtained. Specific activity: 14.3 $\mu$moles of hydrolysed hippuryl-L-arginine/minute/mg protein.

EXAMPLE 12

0.25 kg of swine pancreas are minced on a meat-chopper and allowed to stand at room temperature overnight. Next day 250 ml of a 0.05 molar tris-HCl buffer /pH 8.5/ are added, the suspension is heated to 60° C. and allowed to stand at this temperature for 20 minutes. After addition of 2 parts by volume of icecold water the mixture is centrifuged. To the supernatant 247 g of ammonium sulfate are added. The suspension is allowed to stand overnight, centrifuged and the precipitate is discarded. The pH of the supernatant is adjusted to 7.0–7.2 and 197 g of ammonium sulfate are added. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 1209 mg of carboxypeptidase B are obtained. Specific activity: 6.4 μmoles of hydrolysed hippuryl-L-arginine/minute/mg protein.

TABLE 2

Effect of the pH value of the buffer used in the thermal treatment (60° C., 20 minutes) of homogenised swine pancreas on the activity of carboxypeptidase B

| pH | Total activity (unit/kg pancreas) | Total protein (mg/kg pancreas) | Specific activity (unit/mg) |
| --- | --- | --- | --- |
| 5.0 | 21348 | 1440 | 14.8 |
| 5.5 | 25808 | 1268 | 20.3 |
| 6.0 | 98333 | 1724 | 57.0 |
| 6.5 | 52767 | 1204 | 43.8 |
| 7.0 | 64882 | 1625 | 39.9 |
| 7.5 | 48400 | 2780 | 17.4 |
| 8.0 | 31632 | 2210 | 14.3 |
| 8.5 | 30753 | 4836 | 6.4 |

EXAMPLE 13

0.25 kg of swine pancreas are minced on a meat-chopper and allowed to stand at room temperature overnight. Next morning 250 ml of a 0.05 molar phosphate buffer /pH 6.0/, are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 340 g/l /408 g/. The suspension is allowed to stand overnight, centrifuged, the precipitate is discarded and the supernatant is saturated with ammonium sulfate to a concentration of 370 g/l /41.1 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 95 mg of carboxypeptidase B are obtained. Specific activity: 56.2 μmoles of hydrolysed hippuryl-L-arginine/minute/mg protein.

EXAMPLE 14

0.2 kg of swine pancreas are minced on a meat-chopper and allowed to stand at room temperature overnight. Next morning 200 ml of a 0.05 molar phosphate buffer /pH 6.0/ are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 330 g/l /330 g/. The suspension is allowed to stand overnight, centrifuged, the precipitate is discarded and the supernatant is saturated with ammonium sulfate to a concentration of 370 g/l /44.8 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 62 mg of carboxypeptidase B are obtained. Specific activity: 89.0 μmoles of hydrolysed hippuryl-L-arginine/minute/mg protein.

EXAMPLE 15

0.25 kg of swine pancreas are minced on a meat-chopper and allowed to stand at room temperature overnight. Next morning 250 ml of a 0.05 molar phosphate buffer /pH 6.0/ are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 320 g/l /386 g/. The suspension is allowed to stand overnight, centrifuged, the precipitate is discarded and the supernatant is saturated with ammonium sulfate to a concentration of 370 g/l /65 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 106.5 mg of carboxypeptidase B are obtained. Specific activity: 95.5 μmoles of hydrolysed hippuryl-L-arginine/minute/mg protein.

EXAMPLE 16

0.2 kg of swine pancreas are minced on a meat-chopper and allowed to stand at room temperature overnight. Next morning 200 ml of a 0.05 molar phosphate buffer /pH 6.0/ are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 310 g/l /310 g/. The suspension is allowed to stand overnight, centrifuged, the precipitate is discarded and the supernatant is saturated with ammonium sulfate to a concentration of 370 g/l /67.2 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 135 mg of carboxypeptidase B are obtained. Specific activity: 44.3 μmoles of hydrolysed hippuryl-L-arginine/minute/mg protein.

EXAMPLE 17

0.25 kg of swine pancreas are minced on a meat-chopper and allowed to stand at room temperature overnight. Next morning 250 ml of a 0.05 molar phosphate buffer /pH 6.0/ are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 320 g/l /386.4 g/. The suspension is allowed to stand overnight, centrifuged, the precipitate is discarded and the supernatant is saturated with ammonium sulfate to a concentration of 360 g/l /52 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 76 mg of carboxypeptidase B are obtained. Specific activity: 123.8 μmoles of hydrolysed hippuryl-L-arginine/minute/mg protein.

EXAMPLE 18

0.25 kg of swine pancreas are minced on a meat-chopper and allowed to stand at room temperature overnight. Next morning 250 ml of a 0.05 molar phosphate buffer /pH 6.0/ are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 320 g/l /386.4 g/. The suspension is allowed to stand overnight, centrifuged, the precipitate is discarded and the supernatant is saturated with ammonium sulfate to a concentration of 350 g/l /39 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 45 mg of carboxypeptidase B are obtained. Specific activity: 286.7 μmoles of hydrolysed hippuryl-L-arginine/minute/mg protein.

EXAMPLE 19

0.25 kg of swine pancreas are minced on a meat-chopper and allowed to stand at room temperature overnight. Next morning 250 ml of a 0.05 molar phosphate buffer /pH 6.0/ are added, the suspension is heated to 60° C. and allowed to stand at this temperature for 20 minutes. To the mixture 2 parts by volume of icecold water are added and it is centrifuged. The supernatant is saturated with ammonium sulfate to a concentration of 320 g/l /386.4 g/. The suspension is allowed to stand overnight, centrifuged, the precipitate is discarded and the supernatant is saturated with ammonium sulfate to a concentration of 340 g/l //26 g/. The suspension is allowed to stand overnight and centrifuged. The precipitate is dissolved in a small amount of cold /+4° C./ tris-HCl buffer and dialysed against distilled water until the salt is removed. After dialysis the solution is filtered and frozen. Thus 25.5 mg of carboxypeptidase B are obtained. Specific activity: 195.8 μmoles of hydrolysed hippuryl-L-arginine/minute/mg protein.

TABLE 3

Effect of fractionation with ammonium sulfate on the activity of carboxypeptidase B

| Ammonium sulfate concentration (g/l) | | Total activity (unit/kg pancreas) | Total protein (mg/kg pancreas) | Specific activity (unit/mg) |
| --- | --- | --- | --- | --- |
| 1st saturation | 2nd saturation | | | |
| 340 | 370 | 21373 | 380 | 56.2 |
| 330 | 370 | 27670 | 310 | 89.0 |
| 320 | 370 | 40697 | 426 | 95.5 |
| 310 | 370 | 29914 | 675 | 44.3 |
| 320 | 360 | 37629 | 304 | 123.8 |
| 320 | 350 | 51610 | 180 | 286.7 |
| 320 | 340 | 19977 | 102 | 195.8 |

EXAMPLE 20

1 kg of bovine pancreas are minced on a meat-chopper and allowed to stand at room temperature overnight. Next morning 1 liter of a 0.05 molar phosphate buffer /pH 6.0/ are added, the suspension is heated to 60° C. and allowed to stand at this temperature for 20 minutes. To the mixture 2 parts by volumes /3.8 l/ of icecold water are added and it is centrifuged. The supernatant is saturated with ammonium sulfate to a concentration of 320 g/l /1.6 kg/. The suspension is allowed to stand overnight and centrifuged. The precipitate is discarded and the supernatant is saturated with ammonium sulfate to a concentration of 350 g/l /165 g/. The suspension is allowed to stand overnight and centrifuged. The precipitate is dissolved in a small amount of cold /+4° C./ tris-HCl buffer /pH 7.0/ and dialysed against distilled water until the salt is removed. After dialysis the solution is filtered, 406 mg of sodium chloride are added and the mixture is frozen. Thus 238.7 mg of carboxypeptidase B are obtained. Specific activity: 15.4 μmoles of hydrolysed hippuryl-L-arginine/minute/mg protein.

EXAMPLE 21

1 g of Akrilex C-100 xerogel/carboxy content 6.2±0.3 m-equiv./g/ are suspended in 50 ml of a 0.1 molar potassium phosphate buffer solution /pH 7.0/ whereupon to the suspension a solution of 2 g of N-cyclohexyl-N'-[2-/4-morpholinyl/-ethyl]-carbodiimide-methyl-p-toluene sulfate in 20 ml of a cold /+4° C./ buffer is added on an icecold water-bath under constant stirring. The reaction mixture is stirred for 10 minutes whereupon 31 ml of an aqueous carboxypeptidase B solution/concentration 16.45 mg/ml/ are added. The specific activity amounts to 17 μmoles of hydrolysed hippuryl-L-arginine/minute/mg protein. The reaction time is 48 hours and the mixture is stirred twice for 6 hours each. The gel is separated and washed three times with 100 ml of a 0.1 molar potassium phosphate buffer /pH 7.0/ each, three times with 100 ml of a 0.1 molar potassium phosphate buffer /pH 7.0/ comprising 1 mole of sodium chloride each and three times with 100 ml of a 0.1 molar potassium phosphate buffer /pH 7.0/ each. The gel is finally washed five times with 200 ml of distilled water each. The salt-free gel is liophylised. Yield 1.6 g. Activity 630 μmoles of hydrolysed hippuryl-L-arginine/minute/g dry substance.

EXAMPLE 22

1 g of Akrilex C-100 xerogel/carboxy content 6.2±0.3 m-equiv./g/ are suspended in 50 ml of a 0.1 molar potassium phosphate buffer solution /pH 7.0/ whereupon to the suspension a solution of 1 g of N-cyclohexyl-N'-[2-/4-morpholinyl/-ethyl]-carbodiimide-methyl-p-toluene sulfate in 20 ml of a cold /+4° C./ buffer is added on an icecold water-bath under constant stirring. The reaction mixture is stirred for 10 minutes whereupon 31 ml of an aqueous carboxypeptidase B solution/concentration 16.45 mg/ml/ are added. The specific activity amounts to 17 μmoles of hydrolysed hippuryl-L-arginine/minute/mg protein. The reaction time is 48 hours and the mixture is stirred twice for 6 hours each. The gel is separated and washed three times with 100 ml of a 0.1 molar potassium phosphate buffer /pH 7.0/ each, three times with 100 ml of a 0.1 molar potassium phosphate buffer /pH. 7.0/ comprising 1 mole of sodium chloride each, and three times with 100 ml of a 0.1 molar potassium phosphate buffer /pH 7.0/.each. The gel is finally washed five times with 200 ml of distilled water each. The salt-free gel is liophylised. Yield 1.43 g. Activity 690 μmoles of hydrolysed hippuryl-L-arginine/minute/g dry substance.

EXAMPLE 23

1 g of Akrilex C-100 xerogel/carboxy content 6.2±0.3 m-equiv./g/ are suspended in 50 ml of a 0.1 molar potassium phosphate buffer solution /pH 7.0/ whereupon to the suspension a solution of 2 g of N-cyclohexyl-N'-[2-/4-morpholinyl/-ethyl]-carbodiimide-methyl-p-toluene sulfate in 20 ml of a cold /+4° C./ buffer is added on an icecold water-bath under constant stirring. The reaction mixture is stirred for 10 minutes whereupon 15.5 ml of an aqueous carboxypeptidase B solution/concentration 16.45 mg/ml/ are added. The specific activity amounts to 17 μmoles of hydrolysed hippuryl-L-arginine/minute/mg protein. The reaction time is 48 hours and the mixture is stirred twice for 6 hours each. The gel is separated and washed three times with 100 ml of a 0.1 molar potassium phosphate buffer /pH 7.0/ each, three times with 100 ml of a 0.1 molar potassium phosphate buffer /pH 7.0/ comprising 1 mole of sodium chloride each and three times with 100 ml of a 0.1 molar potassium phosphate buffer /pH 7.0/ each. The gel is finally washed five times with 200 ml of distilled water each. The salt-free gel is liophylised. Yield 1.6 g. Activity 880 μmoles of hydrolysed hippuryl-L-arginine/minute/g dry substance.

EXAMPLE 24

1 g of Akrilex C-100 xerogel/carboxy content 6.2±0.3 m-equiv./g/ are suspended in 50 ml of a 0.1 molar potassium phosphate buffer solution /pH 7.0/ whereupon to the suspension a solution of 2 g of N-cyclohexyl-N'-[2-/4-morpholinyl/-ethyl]-carbodiimide-methyl-p-toluene sulfate in 20 ml of a cold /+4° C./ buffer is added on an icecold water-bath under constant stirring. The reaction mixture is stirred for 10 minutes whereupon 62 ml of an aqueous carboxypeptidase B solution/concentration 16.45 mg/ml/ are added. The specific activity amounts to 17 μmoles of hydrolysed hippuryl-L-arginine/minute/mg protein. The reaction time is 48 hours and the mixture is stirred twice for 6 hours each. The gel is separated and washed three times with 100 ml of a 0.1 molar potassium phosphate buffer /pH 7.0/ each, three times with 100 ml of a 0.1 molar potassium phosphate buffer /pH 7.0/ comprising 1 mole of sodium chloride each, and three times with 100 ml of a 0.1 molar potassium phosphate buffer /pH 7.0/ each. The gel is finally washed five times with 200 ml of distilled water each. The salt-free gel is liophylised. Yield 1.55 g. Activity 740 μmoles of hydrolysed hippuryl-L-arginine/minute/g dry substance.

centrifuging or filtering the resultant mixture to obtain a supernatant, adding 300–320 g/l of ammonium sulfate to the supernatant to obtain a suspension, centrifuging or filtering the suspension to obtain a supernatant, precipitating a fraction comprising active carboxypeptidase B enzyme by adding 10–80 g/l of ammonium sulfate to the supernatant, centrifuging or filtering to separate the precipitate and dissolving the precipitate containing carboxypeptidase B in water or a buffer solution, and dialysing the solution against water or a buffer solution, and storing the dialysed solution containing isolated carboxypeptidase B in frozen state.

2. The process of claim 1, wherein the pH of the buffer used to dilute the autolysate is 6.0–7.0.

3. The process of claim 1, wherein the thermal treatment is at 50–65 degrees centigrade for 15–25 minutes.

4. The process of claim 1, wherein the fraction containing the active carboxypeptidase B enzyme is precipitated by adding 25–35 g/l of ammonium sulfate.

5. The process of claim 1, wherein the carboxypeptidase B isolated is immobilized by treating a polymer gel comprising at least 0.1 m-equiv./g of functional carboxy groups and prepared from acrylic acid and/or methacrylic acid or acrylic amide and/or methacrylic amide with a carbodiimide compound being water soluble or soluble in organic solvents at a temperature below 0 degrees centigrade to activate the polymer gel, applying onto the thus activated polymer gel the isolated carboxypeptidase B enzyme from a buffer solution having a pH of 4.5–8.5, washing the resultant immobilized carboxypeptidase B enzyme, and storing the enzyme in aqueous suspension at 0–4 degrees centigrade and drying the enzyme.

6. The process of claim 5, wherein the buffer solution from which the carboxypeptidase B enzyme is applied to the activated polymer gel has a pH of 6.0–7.0.

7. Process according to claim 5 which comprises using the polymer gel, carbodiimide and carboxypeptidase B enzyme in a ratio of 1:1–2:0.25–1.

8. The process of claim 5, wherein the ratio is 1:2:0.25.

TABLE 4

| Immobilization of carboxypeptidase B ||||||||||||
| Composition of reaction mixture ||| Activity of product (unit/g xerogel) | Immobilized activity || Immobilized protein || Recovered dissolved activity || Loss of activity || Specific activity ||
| 1*AC-100 (g) | 2*CMC (g) | 3*CPB (g) | | unit | % | unit | % | unit | % | unit | % | unit | % |
|---|---|---|---|---|---|---|---|---|---|---|---|---|---|
| 1 | 2 | 510 | 630 | 1008 | 11.6 | 313.7 | 61.5 | 207 | 2.4 | 7444.1 | 86 | 3.21 | 19.51 |
| 1 | 1 | 510 | 690 | 987 | 11.4 | 328 | 64.3 | 285 | 3.3 | 7387.8 | 85.3 | 3.00 | 18.23 |
| 1 | 2 | 255 | 880 | 1408 | 32.5 | 102 | 40 | 73.3 | 1.7 | 2848.3 | 65.8 | 13.80 | 83.89 |
| 1 | 2 | 1020 | 740 | 1147 | 6.6 | 655.6 | 64.3 | 371.9 | 2.1 | 15799.1 | 91.3 | 1.75 | 10.63 |

1*AC-100, Akrilex C-100;
2*CMC, N—cyclohexyl-N—[2-(4-morpholinyl)-ethyl]-carbodiimide-methyl-p-toluenesulfonate;
3*CPB, carboxypeptidase B;
4*the specific activity of the dissolved enzyme is regarded to be 100%.

What we claim is:

1. A process for the isolation of carboxypeptidase B enzyme from mammal pancreas which comprises preparing homogenized pancreas and autolysing the homogenized pancreas, diluting the resultant autolysate in a ratio of 1:1 with a buffer having a pH of 5.0–8.5 to obtain a mixture, subjecting the mixture to thermal treatment at 50–75 degrees centigrade for 5–30 minutes,